United States Patent
Lee et al.

(10) Patent No.: US 10,663,405 B2
(45) Date of Patent: May 26, 2020

(54) RAMAN PROBE AND BIO-COMPONENT ANALYZING APPARATUS USING THE SAME

(71) Applicant: SAMSUNG ELECTRONICS CO., LTD., Suwon-si (KR)

(72) Inventors: Woochang Lee, Anyang-si (KR); Ho Jun Chang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/281,432

(22) Filed: Feb. 21, 2019

(65) Prior Publication Data

US 2019/0257761 A1 Aug. 22, 2019

(30) Foreign Application Priority Data

Feb. 21, 2018 (KR) .................. 10-2018-0020575

(51) Int. Cl.

| | |
|---|---|
| *G01N 21/65* | (2006.01) |
| *A61B 5/145* | (2006.01) |
| *A61B 5/1455* | (2006.01) |
| *G01J 3/02* | (2006.01) |
| *G01J 3/44* | (2006.01) |

(52) U.S. Cl.
CPC .......... *G01N 21/65* (2013.01); *A61B 5/1455* (2013.01); *A61B 5/14532* (2013.01); *G01J 3/0208* (2013.01); *G01J 3/0216* (2013.01); *G01J 3/0227* (2013.01); *G01J 3/4412* (2013.01); *A61B 2562/0247* (2013.01)

(58) Field of Classification Search
CPC .. G01N 21/65; A61B 5/14532; A61B 5/1455; A61B 2562/0247; G01J 3/44
See application file for complete search history.

(56) References Cited

U.S. PATENT DOCUMENTS

| | | | | |
|---|---|---|---|---|
| 3,757,770 | A * | 9/1973 | Brayshaw | A61B 5/0031 600/302 |
| 5,593,899 | A * | 1/1997 | Wilson | A61B 5/0059 422/79 |
| 6,223,063 | B1 | 4/2001 | Chaiken et al. | |
| 6,882,872 | B2 | 4/2005 | Uchida et al. | |
| 7,598,483 | B2 | 10/2009 | Uchida | |

(Continued)

FOREIGN PATENT DOCUMENTS

| | | | | |
|---|---|---|---|---|
| EP | 3485802 A1 * | 6/2018 | | A61B 5/00 |
| JP | 2004-290226 A | 10/2004 | | |

(Continued)

*Primary Examiner* — Maurice C Smith
(74) *Attorney, Agent, or Firm* — Sughrue Mion, PLLC

(57) ABSTRACT

Provided are a Raman probe and a bio-component analyzing apparatus using the same. The Raman probe according to an embodiment of the present disclosure may include: a probe head having a concave part configured to receive skin of an object being inserted into the concave part when the probe head comes into contact with the skin of the object; a light source part configured to emit light onto the skin inserted into the concave part; and a light collector formed above the concave part and configured to collect Raman scattered light from the skin inserted into the concave part. The light source part may be disposed on a side of at least one of the light collector and the concave part.

11 Claims, 6 Drawing Sheets

(56) References Cited

U.S. PATENT DOCUMENTS

| | | | |
|---|---|---|---|
| 7,873,397 B2 | 1/2011 | Higgins et al. | |
| 8,315,681 B2 | 11/2012 | Kanayama et al. | |
| 9,036,970 B2 | 5/2015 | Guyon | |
| 9,717,425 B2 | 8/2017 | Kiani et al. | |
| 2002/0188223 A1* | 12/2002 | Perez | A61B 5/14514 |
| | | | 600/573 |
| 2004/0175826 A1 | 9/2004 | Maor | |
| 2005/0248758 A1* | 11/2005 | Carron | G01J 3/02 |
| | | | 356/301 |
| 2007/0017666 A1 | 1/2007 | Goenka et al. | |
| 2013/0229651 A1 | 9/2013 | Ouwerkerk et al. | |
| 2017/0119290 A1* | 5/2017 | Cai | A61B 5/14532 |
| 2018/0064069 A1* | 3/2018 | Meissner | A61D 1/005 |
| 2019/0150746 A1* | 5/2019 | Kim | A61B 5/0082 |

FOREIGN PATENT DOCUMENTS

| | | | | |
|---|---|---|---|---|
| JP | 2004290226 | * | 10/2004 | A61B 5/145 |
| JP | 5095468 B2 | | 10/2009 | |

\* cited by examiner

RAMAN PROBE AND BIO-COMPONENT ANALYZING APPARATUS USING THE SAME

CROSS-REFERENCE TO RELATED APPLICATION

This application claims priority from Korean Patent Application No. 10-2018-0020575, filed on Feb. 21, 2018, in the Korean Intellectual Property Office, the entire disclosure of which is incorporated herein by reference.

BACKGROUND

1. Field

The following description relates to a Raman probe and a bio-component analyzing apparatus using the same.

2. Description of the Related Art

Non-invasive glucose sensors, using spectroscopic analysis techniques such as Raman spectroscopy, may improve convenience of diabetic patients who need to draw blood regularly, or people at risk of metabolic diseases. Particularly, such non-invasive analysis techniques may be used to predict a signal of a blood component by analyzing interstitial fluid present in a dermal layer based on each individual skin spectrum. However, a considerable amount of incident light disappears while passing along an incident path (e.g., dead skin cells, epidermis layer, dermis layer, etc.), and a signal derived from biomolecules (e.g., lipid, protein, etc.) is mixed therewith, such that the obtained skin Raman spectrum has greater background noise compared to a signal of a target material (e.g., glucose).

SUMMARY

One or more example embodiments provide a Raman probe and a bio-component analyzing apparatus using the same.

According to an aspect of an example embodiment, there is provided a Raman probe including: a probe head having a concave part configured to receive skin of an object being inserted into the concave part when the probe head comes into contact with the skin of the object; a light source part configured to emit light onto the skin inserted into the concave part; and a light collector formed above the concave part and configured to collect Raman scattered light from the skin inserted into the concave part. The light source part may be disposed on a side of at least one of the light collector and the concave part.

The light source part may be further configured to emit light onto the skin, which is inserted into the concave part, at a predetermined angle with respect to a vertical axis of the light collector.

The light source part may include: a light source configured to emit the light; and a filter configured to allow a specific wavelength of the light to pass through among a plurality of wavelengths of the light emitted by the light source.

The light source part may further include a reflection mirror configured to reflect the light emitted by the light source to direct the light toward a desired position.

The light collector may include: a first lens configured to collect the Raman scattered light; and a filter configured to remove a light component having a same wavelength band as the light emitted by the light source part among the collected Raman scattered light.

The first lens may be one of a collection lens and a collimating lens.

The filter may be one of a notch filter and a long-pass filter.

The light collector may further include: a second lens configured to focus the light having passed through the filter; and a fiber configured to transmit the focused light to an outside.

The Raman probe may further include a pressure measurer configured to measure contact pressure of the skin.

The pressure measurer may be formed at the probe head.

The Raman probe may further include a notification information generator configured to determine whether the skin is inserted into the concave part based on the measured contact pressure, and to generate notification information based on the determination.

The Raman probe may further include an output interface configured to output the generated notification information.

BRIEF DESCRIPTION OF THE DRAWINGS

The above and/or other aspects will become apparent and more readily appreciated from the following description of exemplary embodiments, taken in conjunction with the accompanying drawings in which.

DETAILED DESCRIPTION

Figure 1:
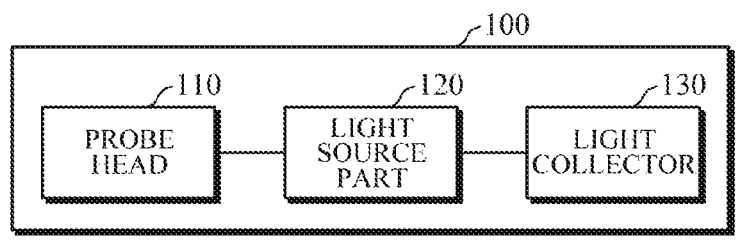
FIG. 1 is a block diagram illustrating an example of a Raman probe.

Hereinafter, example embodiments of the present disclosure will be described in detail with reference to the accompanying drawings. It should be noted that, in the drawings, the same reference symbols refer to same parts although illustrated in other drawings. In the following description, a detailed description of known functions and configurations incorporated herein will be omitted when it may obscure the subject matter of the present invention.

Process steps described herein may be performed differently from a specified order, unless a specified order is clearly stated in the context of the disclosure. That is, each step may be performed in a specified order, substantially at the same time, in a reverse order, or in any other order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

It will be understood that, although the terms "first," "second," etc. may be used herein to describe various elements, these elements should not be limited by these terms. These terms do not necessarily imply order, preference, or precedence and are only used to distinguish one element from another. Any references to singular may include plural unless expressly stated otherwise in the present specification, it should be understood that the terms, such as "including" or "having," etc., are intended to indicate the existence of the features, numbers, steps, actions, components, parts, or combinations thereof disclosed in the specification, and are not intended to preclude the possibility that one or more other features, numbers, steps, actions components, parts, or combinations thereof may exist or may be added.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware (e.g., a circuit, a microchip, a processor, etc.), software (e.g., instructions, code, a program, an application, firmware, etc.), or a combination of both.

Throughout the drawings and the detailed description, unless otherwise described, the same drawing reference numerals will be understood to refer to the same elements, features, and structures. The relative size and depiction of these elements may be exaggerated for clarity, illustration, and convenience. The word "exemplary" used herein to mean "serving as an example or illustration." Any aspect or design described herein as "exemplary" is not necessarily to be construed as preferred or advantageous over other aspects or designs.

FIG. 1 is a block diagram illustrating an example of a Raman probe.

Referring to FIG. 1, the Raman probe 100 includes a probe head 110, a light source part 120, and a light collector 130.

The probe head 110 may come into contact with the skin of an object (e.g., human body). The probe head 110 may include a concave part (e.g., a recess or an indentation), into which the skin of the object may be inserted when the probe head 110 comes into contact with the skin of the object.

The light source part 120 may emit light onto the skin of the object. To this end, the light source part 120 may include a light source. In one embodiment, the light source may emit light of a predetermined wavelength, e.g., visible light or infrared light, onto a sample (e.g., analysis target). However, the light source is not limited thereto, and wavelengths of light emitted by the light source may vary depending on the purpose of measurement and an analysis target. Further, the light source is not necessarily a single light emitting body, but may be an array of a plurality of light emitting bodies. In the case where the light source is configured as an array of a plurality of light emitting bodies, the plurality of light emitting bodies may emit light of different wavelengths according to the purpose of measurement, or all the light emitting bodies may emit light of the same wavelength. In one embodiment, the light source may be a light emitting diode (LED), a laser diode, or the like. However, this is merely exemplary, and the light source is not limited thereto.

In one embodiment, the light source part 120 may further include a filter (e.g., clean-up filter, band-pass filter, etc.) for selecting light of a specific wavelength (e.g., a specific wavelength band) and/or an optical element (e.g., reflection mirror, etc.) for directing the emitted light toward a desired position on the skin of an object.

The light collector 130 may collect Raman scattered light from the skin inserted into the concave part. To this end, the light collector 130 may include a filter (e.g., notch filter, long-pass filter, etc.), a lens (e.g., collection lens, collimating lens, focusing lens, etc.), a fiber, a waveguide, a grating, and the like.

The light collector 130 may be formed above the concave part to collect Raman scattered light from the skin inserted into the concave part; and the light source part 120 may be formed on a side of the light collector 130 or a side of the concave part to minimize interference between the emitted light and Raman scattered light.

Although FIG. 1 illustrates the Raman probe 100 including one light source part 120, the Raman probe 100 is not limited thereto. That is, the Raman probe 100 may include two or more light source parts 120, in which case the two or more light source parts 120 may be formed on a side of the light collector 130 or a side of the concave part to surround the light collector 130 or the concave part.

Figure 2:
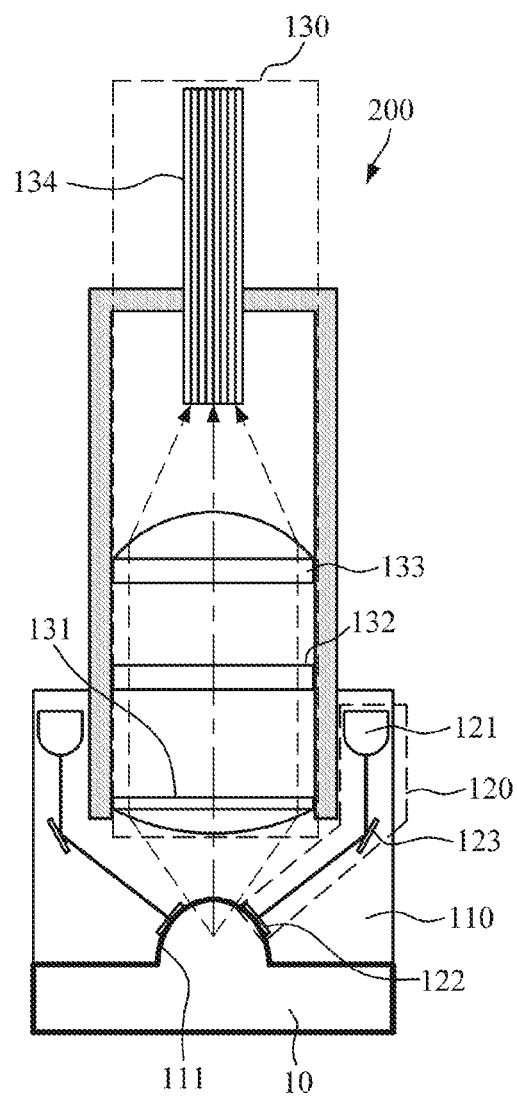
FIG. 2 is a diagram illustrating an example of a structure of a Raman probe.

FIG. 2 is a diagram illustrating an example of a structure of a Raman probe. The Raman probe 200 of FIG. 2 may be an example of the Raman probe 100 of FIG. 1.

Referring to FIG. 2, the Raman probe 200 includes a probe head 110, a light source part 120, and a light collector 130.

The probe head 110 may come into contact with skin 10 of an object (e.g., human body). The probe head 110 may include a concave part 111, into which the skin 10 of the object may be inserted when the probe head 110 comes into contact with the skin 10 of the object. In this case, a cross-section of the concave part 111 may be formed in an arch shape or a semi-circular shape.

The light source part 120 may be formed on a side of the light lector 130 and may emit light onto the skin 10 of the object inserted into the concave part 111. To this end, the light source part 120 may include a light source 121, a filter 122, and a reflection mirror 123.

The light source 121 may emit light of a specific wavelength, e.g., visible light or infrared light.

The filter 122 may allow light of a specific wavelength to pass among lights emitted by the light source 121. In one embodiment, the filter 122 may be a clean-up filter or a band-pass filter.

The reflection mirror 123 may reflect light emitted by the light source 121 to direct the emitted light toward a desired position. In one embodiment, the reflection minor 123 may allow the light emitted by the light source to be emitted onto the skin 10, inserted into the concave part 111, at a predetermined angle (e.g., angle of 50 degrees or greater) with respect to a vertical axis of the light collector 130.

The light collector 130 may be formed concave part 111 to collect Raman scattered light from the skin 10 inserted into the concave part 111. To this end, the light collector 130 may include a first lens 131, a filter 132, a second lens 133, and a fiber 134.

The first lens 131 may collect Raman scattered light from the skin 10 inserted into the concave part 111. In one embodiment, the first lens 131 may be a collection lens or a collimating lens.

The filter 132 may remove a light component having the same wavelength band as the light emitted by the light source part 120. In one embodiment, the filter 132 may be a notch filter or a long-pass filter.

The second lens 133 may focus light, having passed through the filter 132, onto the fiber 134, and the fiber 134 may transmit the focused light to the outside (e.g., other device, other component, etc.). In one embodiment, the second lens 133 may be a focusing lens.

Figure 3:
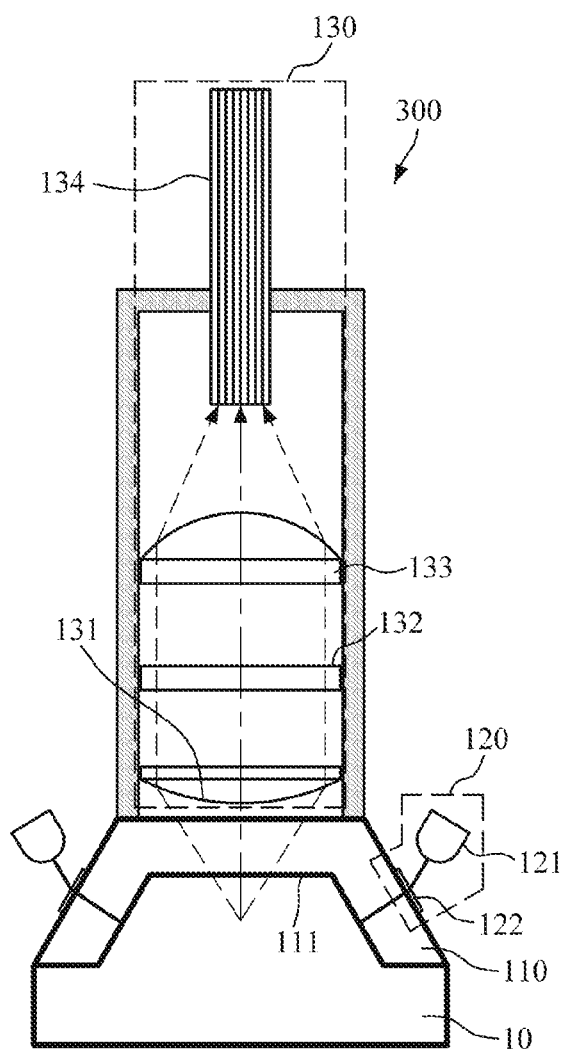
FIG. 3 is a diagram illustrating another example of a structure of a Raman probe.

FIG. 3 is a diagram illustrating another example of a structure of a Raman probe. The Raman probe 300 of FIG. 3 may be another example of the Raman probe 100 of FIG. 1.

Referring to FIG. 3, the Raman probe 300 includes a probe head 110, a light source part 120, and a light collector 130.

The probe head 110 may come into contact with skin 10 of an object. The probe head 110 may include a concave part 111, into which the skin 10 of the object may be inserted when the probe head 110 comes into contact with the skin 10 of the object. 1n this case, the cross-section of the concave part 111 may be formed in a trapezoidal shape. Thus, the hollow space of the concave part 111 may be shaped like a bowl with its radius increasing towards the skin 10.

The light source part 120 may be formed on a side surface of the concave part 111 and may emit light onto the skin 10 of the object inserted into the concave part 111. To this end, the light source part 120 may include alight source 121 and a filter 122.

The light source 121 may emit light of a specific wavelength, e.g., visible light or infrared light, onto the skin 10 inserted into the concave part 111. In one embodiment, the light source 121 may emit light onto the skin 10, inserted into the concave part 111, at a predetermined angle (e.g., angle of 50 degrees or greater) with respect to a vertical axis of the light collector 130.

The filter 122 may allow light of a specific wavelength to pass among lights emitted by the light source 121. In one embodiment, the filter 122 may be a clean-up filter or a band-pass filter.

The light collector 130 may be formed above the concave part 111 to collect Raman scattered light from the skin inserted into the concave part 111. To this end, the light collector 130 may include a first lens 131, a filter 132, a second lens 133, and a fiber 134.

The first lens 131 may collect Raman scattered light from the skin 10 inserted into the concave part 111. In one embodiment, the first lens 131 may be a collection collimating lens.

The filter 132 may remove a light component having the same wavelength band as the light emitted by the light source 120. In one embodiment, the filter 132 may be a notch filter or a long-pass filter.

The second lens 133 may focus light, having passed through the filter 132, onto the fiber 134, and the fiber 134 may transmit the focused light to the outside. In one embodiment, the second lens 133 may be a focusing lens.

Figure 4:
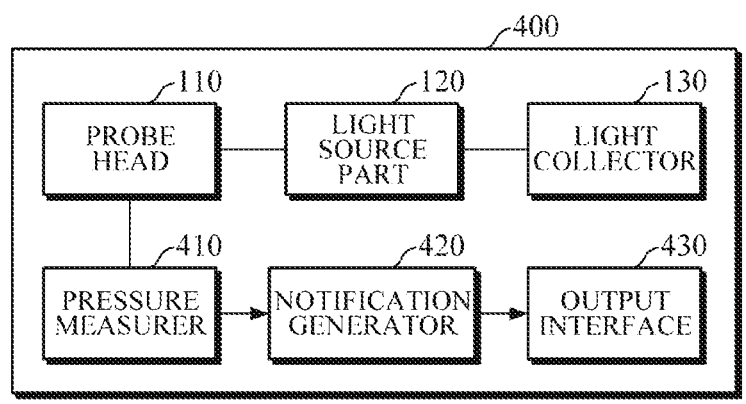
FIG. 4 is a block diagram illustrating another example of a Raman probe.

FIG. 4 is a block diagram illustrating another example of a Raman probe.

Referring to FIG. 4, the Raman probe 400 includes a probe head 110, a light source part 120, a light collector 130, a pressure measurer 410, a notification information generator 420, and an output interface 430. Here, the probe head 110, the light source part 120, and the light collector 130 are described above with reference to FIGS. 1 to 3, such that detailed description thereof will be omitted.

The pressure measurer 410 may be formed at the probe head 110, and may measure contact pressure between the skin of an object and the probe head 110. There is no restriction on the position of the probe head 110 at which the pressure measurer 410 is formed, as long as the position does not affect emission of light and collection of Raman scattered light. That is, as long as emission of light and collection of Raman scattered light are not affected, the pressure measurer 410 may be formed at a concave part 111, or may be formed in a region of the probe head 110 other than the concave part 111.

The notification information generator 420 may determine whether the skin of an object is inserted into the concave part 111 based on the contact pressure measured by the pressure measurer 410. In one embodiment, the notification information generator 420 may determine whether the contact pressure, measured by the pressure measurer 410, exceeds a predetermined threshold value. In response to the contact pressure exceeding the predetermined threshold value, the notification information generator 420 may determine that the skin of the object is inserted into the concave part 111. By contrast, in response to the contact pressure being less than or equal to the predetermined threshold value, the notification information generator 420 may determine that the skin of the object is not inserted into the concave part 111. In this case, the predetermined threshold value may vary depending on the position of the pressure measurer 410. That is, in the case where the pressure measurer 410 is formed in a region of the probe head 110 other than the concave part 111, the predetermined threshold value may be set to a relatively high value as compared to a case where the pressure measurer 410 is formed at the concave part 111.

The notification information generator 420 may generate notification information according to a result of determination on whether the skin is inserted into the concave part 111. For example, upon determining that the skin is not inserted into the concave part 111, the notification information generator 420 may generate notification information e. "press the probe against the skin", etc.) for inducing the skin to be properly inserted into the concave part 111. Further, upon determining that the skin is inserted into the concave part 111, the notification information generator 420 may generate notification information (e.g., "measurement is ready to be taken," etc.) for indicating that measurement is ready to start.

The output interface 430 may output the notification information, generated by the notification information generator 420, to the outside. In one embodiment, the output interface 430 may output the generated notification information by using at least one of an acoustic method, a visual method, and a tactile method. To this end, the output interface 430 may include a display, a speaker, a vibrator, and the like.

Figure 5:
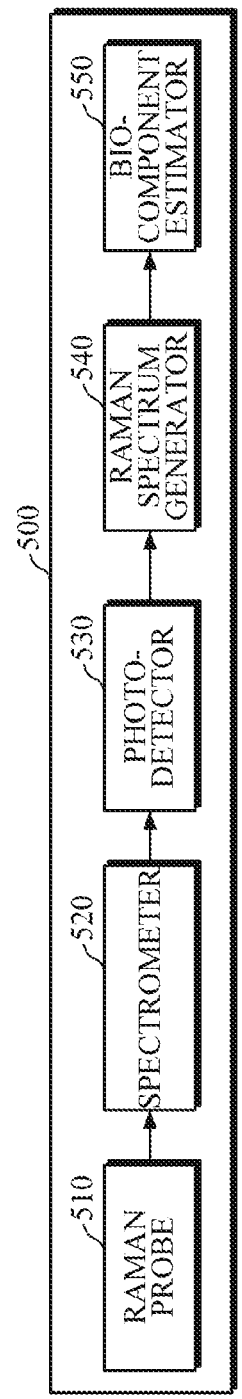
FIG. 5 is a block diagram illustrating an example of a bio-component analyzing apparatus.

FIG. 5 is a block diagram illustrating an example of a bio-component analyzing at s. Referring to FIG. 5, the bio-component analyzing apparatus 500 includes a Raman probe 510, a spectrometer 520, a photodetector 530, a Raman spectrum generator 540, and a bio-component estimator 550. Here, the Raman probe 510 is the same as the Raman probes 100 and 400 described above with reference to FIGS. 1 to 4, such that detailed description thereof will be omitted.

The spectrometer 520 may spatially separate the Raman red light, collected by the Raman probe 510, into different wavelengths. To this end, the spectrometer 520 may include a prism, a grating, and the like.

The photodetector 530 may receive the Raman scattered light which is separated into wavelengths by the spectrometer 520. In one embodiment, the photodetector 530 may be a photo diode, a photo transistor (PTr), a charge-coupled device (CCD), or the like. The photodetector 530 is not necessarily a single device, and may be an array of a plurality of devices.

The Raman spectrum generator 540 may generate a Raman spectrum based on the light received by the photodetector 530.

The bio-component estimator 550 may estimate a bio-component of an object by analyzing the Raman spectrum. Here, examples of the bio-component include: blood components such as blood glucose, cholesterol, triglyceride, protein, uric acid, and the like; and skin components such as collagen, keratin, elastin, and the like.

Figure 6:
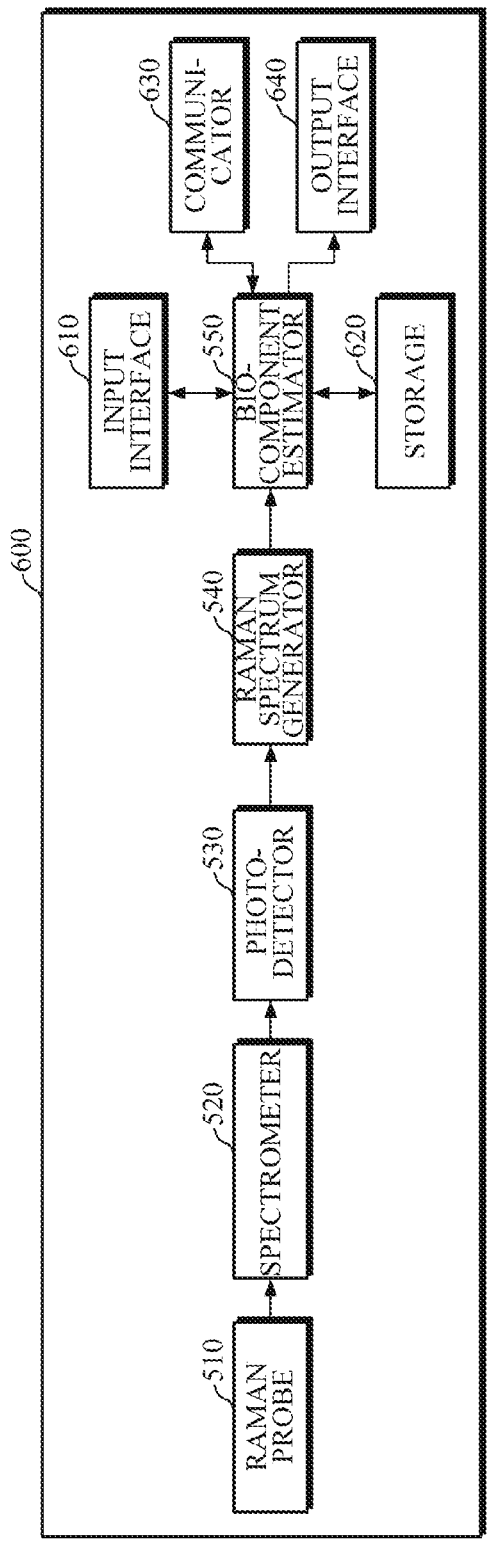
FIG. 6 is a block diagram illustrating another example of a bio-component analyzing apparatus.

FIG. 6 is a block diagram illustrating another example of a bio-component analyzing apparatus.

Referring to FIG. 6, the bio-component analyzing apparatus 600 includes a Raman probe 510, a spectrometer 520, a photodetector 530, a Raman spectrum generator 540, a bio-component estimator 550, an input interface 610, a storage 620, a communicator 630, and an output interface 640. Here, the Raman probe 510, the spectrometer 520, the photodetector 530, the Raman spectrum generator 540, and the bio-component estimator 550 are described above with reference to FIG. 5, such that detailed description thereof will be omitted.

The input interface 610 may receive input of various operation signals from a user. In one embodiment, the input interface 610 may include a keypad, a dome switch, a touch pad (e.g., static pressure/capacitance), a jog wheel, a jog switch, a hardware (H/W) button, and the like. Particularly, the touch pad, which forms a layer structure with a display, may be called a touch screen.

The storage 620 may store programs or commands for operation of the bio-component analyzing apparatus 600, and may store data input to and output from the bio-component analyzing apparatus 600. Further, the storage 620 may store a Raman spectrum of an object which is generated by the Raman spectrum generator 540, and bio-information of an object which is estimated by the bio-component estimator 550.

The storage 620 may include at least one storage medium of a flash memory type memory, a hard disk type memory, a multimedia card micro type memory, a card type memory (e.g., an Secure Digital (SD) memory, an xD-Picture Card memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disc, and the like. Further, the bio-component analyzing apparatus 600 may operate an external storage medium, such as web storage and the like, which performs a storage function of the storage 620 on the Internet.

The communicator 630 may perform communication with an external device. For example, the communicator 630 may transmit, to the external device, data input by a user through the input interface 610, the Raman spectrum of an object which is generated by the Raman spectrum generator 540, and the bio-information of an object which is estimated by the bio-component estimator 550, and the like; or may receive, from the external device, various data useful for obtaining a Raman spectrum and/or estimating bio-information.

In this case, the external device may be medical equipment using the data input by a user through the input interface 610, the Raman spectrum of an object which is generated by the Raman spectrum generator 540, the bio-information of an object which is estimated by the bio-component estimator 550, and the like, a printer to print out results, or a display to display the results. In addition, the external device may be a digital TV, a desktop computer, a cellular phone, a smartphone, a tablet personal computer (PC), a laptop computer, a personal digital assistant (PDA), a portable multimedia player (PMP), a navigation, an MP3 player, a digital camera, a wearable device, and the like, but is not limited thereto.

The communicator 630 may communicate with an external device by using Bluetooth communication, Bluetooth Low Energy (BLE) communication, Near-Field Communication (NFC), wireless local area network (WLAN) communication, Zigbee communication, Infrared Data Association (IrDA) communication, Wi-Fi Direct (WFD) communication, Ultra-Wideband (UWB) communication, Ant+ communication, Wi-Fi communication, Radio Frequency Identification (RFID) communication, 3G communication, 4G communication, 5G communication, and the like. However, this is merely exemplary and is not intended to be limiting.

The output interface 640 may output the data input by a user through the input interface 610, the Raman spectrum of an object which is generated by the Raman spectrum generator 540, the bio-information of an object which is estimated by the bio-component estimator 550, and the like. In one embodiment, the output interface 640 may output the data input by a user through the input interface 610, the Raman spectrum of an object which is generated by the Raman spectrum generator 540, the bio-information of an object which is estimated by the bio-component estimator 550, and the like, by using at least one of an acoustic method, a visual method, and a tactile method. To this end, the output interface 640 may include a display, a speaker, a vibrator, and the like.

The present disclosure can be realized as a computer-readable code written on a computer-readable recording medium. Code and code segments needed for realizing the present disclosure can be easily deduced by computer programmers of ordinary skill in the art. The computer-readable recording medium may be any type of recording device in which data is stored in a computer-readable manner. Examples of the computer-readable recording medium include a ROM, a RAM, a compact disc read-only memory (CD-ROM), a magnetic tape, a floppy disc, an optical disc, and the like. Further, the computer-readable recording medium can be distributed over a plurality of computer systems connected to a network so that a computer-readable recording medium is written thereto and executed therefrom in a decentralized manner.

The present disclosure has been described herein with regard to example embodiments. However, it will be obvious to those skilled in the art that various modifications can be made without departing from the present disclosure. Therefore, it is to be understood that that the scope of the present disclosure is not limited to the above-mentioned example embodiments, but is intended to include various modifications and equivalents included within the spirit and scope of the appended claims.

What is claimed is:

1. A Raman probe, comprising:
   a probe head having a concave part configured to receive skin of an object being inserted into the concave part when the probe head comes into contact with the skin of the object;
   a light source part disposed on a side of the concave part and configured to emit light onto the skin through the side of the concave part;
   a pressure measurer formed at the probe head and configured to measure contact pressure of the skin; and a light collector formed above a center of the concave part and configured to collect Raman scattered light when the Raman scattered light is scattered from the skin and then passes through the center of the concave part.

2. The Raman probe of claim 1, wherein the light source part is further configured to emit the light onto the skin, which is inserted into the concave part, at a predetermined angle with respect to a vertical axis of the light collector.

3. The Raman probe of claim 1, wherein the light source part comprises:
    a light source configured to emit the light; and
    a filter configured to allow a specific wavelength of the light to pass through among a plurality of wavelengths of the light emitted by the light source.

4. The Raman probe of claim 3, wherein the light source part further comprises a reflection mirror configured to reflect the light emitted by the light source to direct the light toward a desired position.

5. The Raman probe of claim 1, wherein the light collector comprises:
    a first lens configured to collect the Raman scattered light; and
    a filter configured to remove a light component having a same wavelength band as the light emitted by the light source part among the collected Raman scattered light.

6. The Raman probe of claim 5, wherein the first lens is one of a collection lens and a collimating lens.

7. The Raman probe of claim 5, wherein the filter is one of a notch filter and a long-pass filter.

8. The Raman probe of claim 5, wherein the light collector further comprises:
    a second lens configured to focus the light having passed through the filter; and
    a fiber configured to transmit the focused light to an outside.

9. The Raman probe of claim 1 further comprising a notification information generator configured to determine whether the skin is inserted into the concave part based on the measured contact pressure, and to generate notification information based on the determination.

10. The Raman probe of claim 9, further comprising an output interface configured to output the generated notification information.

11. The Raman probe of claim 1, wherein the light source part comprises a first light source configured to emit the light onto the skin through the side of the concave part, and a second light source configured to emit another light onto the skin through another side of the concave part, and
    wherein the light collector is disposed directly above the center of concave part, and between the first light source and the second light source.

* * * * *